US012611514B2

(12) United States Patent
Veasey et al.

(10) Patent No.: US 12,611,514 B2
(45) Date of Patent: Apr. 28, 2026

(54) TRACHEOSTOMY TUBES AND THEIR MANUFACTURE

(71) Applicant: SMITHS MEDICAL INTERNATIONAL LIMITED, Ashford (GB)

(72) Inventors: Neil Steven Veasey, Ashford (GB); Christopher John Woosnam, London (GB); Andrew Thomas Jeffrey, Marsh (GB)

(73) Assignee: ICU MEDICAL INTERNATIONAL LIMITED, Ashford (GB)

( * ) Notice: Subject to any disclaimer, the term of this patent is extended or adjusted under 35 U.S.C. 154(b) by 748 days.

(21) Appl. No.: 17/916,848

(22) PCT Filed: Mar. 17, 2021

(86) PCT No.: PCT/GB2021/000034
§ 371 (c)(1),
(2) Date: Oct. 4, 2022

(87) PCT Pub. No.: WO2021/209733
PCT Pub. Date: Oct. 21, 2021

(65) Prior Publication Data
US 2023/0141119 A1 May 11, 2023

(30) Foreign Application Priority Data
Apr. 17, 2020 (GB) ...................................... 2005619

(51) Int. Cl.
*A61M 16/04* (2006.01)
*A61M 16/08* (2006.01)

(52) U.S. Cl.
CPC .... *A61M 16/0465* (2013.01); *A61M 16/0497* (2013.01); *A61M 16/0816* (2013.01); *A61M 2205/0216* (2013.01); *A61M 2207/10* (2013.01)

(58) Field of Classification Search
CPC .............. A61M 16/04; A61M 16/0427; A61M 16/0429; A61M 16/0434; A61M 16/0443;
(Continued)

(56) References Cited

U.S. PATENT DOCUMENTS

| | | | | | |
|---|---|---|---|---|---|
| 3,395,711 | A | * | 8/1968 | Plzak, Jr. .......... | A61M 16/0465 128/200.26 |
| 3,659,612 | A | * | 5/1972 | Shiley .............. | A61M 16/0443 128/207.15 |

(Continued)

FOREIGN PATENT DOCUMENTS

| | | | | | |
|---|---|---|---|---|---|
| EP | | 2873432 A1 | 11/2013 | | |
| WO | WO-2016110659 A2 | * | 7/2016 | ........ | A61M 16/0465 |
| WO | | 2016198817 A1 | 12/2016 | | |

OTHER PUBLICATIONS

PCT International Search Report for PCT/GB2021/000034 dated Jun. 29, 2021.
PCT Written Opinion for PCT/GB2021/000034 dated Jun. 29, 2021.

*Primary Examiner* — Annette Dixon
(74) *Attorney, Agent, or Firm* — Louis Woo

(57) ABSTRACT

A tracheostomy tube has a machine end coupling (2) of a relatively hard plastics and formed with a retaining ring structure formation (23) at its patient end. This is joined with a tubular shaft (1) of a softer plastics, such as silicone, to form a subassembly (7) by a moulded interconnection of the machine end of the shaft about the retaining formation (23). An enlarged boss (12) at the rear end of the shaft (1) forms a forwardly facing wall (15). The tube also includes a moulded neck flange (5) of a relatively soft plastics with a
(Continued)

central collar (50) having an internal, rearwardly facing wall (59). The boss (12) on the subassembly (7) is bonded into the collar (5) with the wall (15) on the boss abutting the wall (59) on the flange (5).

9 Claims, 8 Drawing Sheets

(58) Field of Classification Search
CPC .......... A61M 16/0445; A61M 16/0465; A61M 16/0475; A61M 16/0479; A61M 16/0488; A61M 16/0497; A61M 16/08; A61M 16/0816; A61M 16/0825; A61M 2205/32; A61M 2207/00; B29C 57/02; B29C 65/48; B29C 65/4895; B29C 66/5344; B29C 66/71; B29C 66/73151; B29C 66/7392; B29K 2021/003; B29K 2027/06; B29K 2069/00; B29K 2075/00; B29L 2023/007; Y10S 128/26; Y10S 128/912; Y10T 156/10; Y10T 29/49826
See application file for complete search history.

(56) References Cited

U.S. PATENT DOCUMENTS

| | | | | | |
|---|---|---|---|---|---|
| 4,033,353 | A | * | 7/1977 | La Rosa ........... | A61M 16/0497 128/207.15 |
| 4,235,229 | A | * | 11/1980 | Ranford ........... | A61M 16/0497 128/207.15 |
| 4,315,505 | A | * | 2/1982 | Crandall ........... | A61M 16/0465 128/207.15 |
| 6,135,110 | A | * | 10/2000 | Roy ................... | A61M 16/0465 128/207.14 |
| 6,135,111 | A | * | 10/2000 | Mongeon .......... | A61M 16/0497 128/207.14 |
| 10,603,455 | B2 | * | 3/2020 | Jeffrey ............. | A61M 16/0488 |
| 2007/0181132 | A1 | | 8/2007 | Worley | |
| 2008/0149108 | A1 | * | 6/2008 | Neame .............. | A61M 16/0427 128/207.14 |
| 2012/0204882 | A1 | * | 8/2012 | Hayman ........... | A61M 16/0465 128/207.14 |
| 2012/0227746 | A1 | * | 9/2012 | Harrington ............. | B29C 57/02 128/207.14 |
| 2012/0247478 | A1 | * | 10/2012 | Harrington ....... | A61M 16/0825 128/207.14 |

* cited by examiner

TRACHEOSTOMY TUBES AND THEIR MANUFACTURE

This invention relates to tracheostomy tubes of the kind comprising a shaft for providing a gas passage to the trachea, a coupling for enabling gas connection with the shaft, and a flange for securing the tube with a patient's neck.

Tracheostomy tubes are used to enable ventilation or respiration of a patient. They are inserted into the trachea via a surgically formed opening in the neck so that one end of the tube locates in the trachea and the other end locates outside the patient adjacent the neck surface. Tracheostomy tubes are generally used for more long-term ventilation or where it is not possible to insert an airway through the mouth or nose. Various types of different tracheostomy tubes are presently available to suit different needs. The tube may be moulded of a soft material, such as a silicone plastics material, where there is a greater risk of trauma to the tracheal lining, such as in paediatric patients or patients with a damaged trachea. Typically, tubes are made by a one-shot moulding process where the shaft of the tube and the flange by which it is secured to the patient are moulded together an integral, one-piece component. The machine end coupling by which gas connection is made to the shaft is separately moulded from a different, harder material and subsequently attached to the machine end of the shaft and flange sub-assembly. The different properties of the materials from which the connector and shaft are made can make it difficult to ensure a secure, leak-proof connection of the coupling to the shaft. Also, the mould tooling required to mould the flange and shaft together is relatively large and expensive. Problems therefore exist in providing tracheostomy tubes with the desired properties that can be used safely and manufactured at low cost.

It is an object of the present invention to provide an alternative tracheostomy tube and a method of manufacturing such a tube.

According to one aspect of the present invention there is provided a tracheostomy tube of the above-specified kind, characterised in that the coupling is of a harder material than the shaft, that the rear, machine end of the shaft is attached with the coupling by material of the shaft flowed around a retaining formation at the patient end of the coupling to form a subassembly by mechanical interlocking of the shaft with the coupling, that the external surface at the rear end of the subassembly is formed with an abutment surface facing towards the forward, patient end of the tube, and that the flange has an attachment portion with an abutment surface facing rearwardly, the abutment surface on the flange abutting the abutment surface on the subassembly so as to prevent forward movement of the subassembly relative to the flange.

The retaining formation is preferably provided by a ring structure extending around the forward end of the coupling, the material of the shaft being flowed in and around the ring structure. The ring structure may include two discs spaced from one another along the length of the coupling. The two discs are preferably spaced from one another by an annular cavity, the forward disc being formed with a plurality of apertures opening through the disc into the cavity. The flange is preferably bonded with the abutment surface on the subassembly. The abutment surface at the rear end of the subassembly is preferably provided by an externally enlarged boss formed with a locating lug arranged to locate in a notch formed in the flange. The shaft may be of a silicone material. The flange may be of a silicone material. The coupling may be of polysulphone.

According to another aspect of the present invention there is provided a method of manufacturing a tracheostomy tube including the steps of: moulding a coupling of relatively hard material and having a retaining formation around its forward, patient end; moulding a shaft of a softer material onto the coupling so that material at the rear, machine end of the shaft flows around the retaining formation to form a subassembly by mechanical interlocking of the shaft with the coupling, the external surface of the rear end of the subassembly being formed with an abutment surface facing forwardly; providing a flange having an attachment portion with an opening and an abutment surface around the opening facing rearwardly; threading the opening on the flange along the shaft from its patient end to its machine end until the abutment surface on the flange abuts the abutment surface on the subassembly; and bonding the flange to the shaft with the engagement of the abutment surfaces and preventing forward movement of the subassembly relative to the flange.

According to a further aspect of the present invention there is provided a tracheostomy tube made by a method according to the above other aspect of the present invention.

A tracheostomy tube and its method of manufacture according to the present invention will now be described by way of example, with reference to the accompanying drawings, in which.

Figure 1:
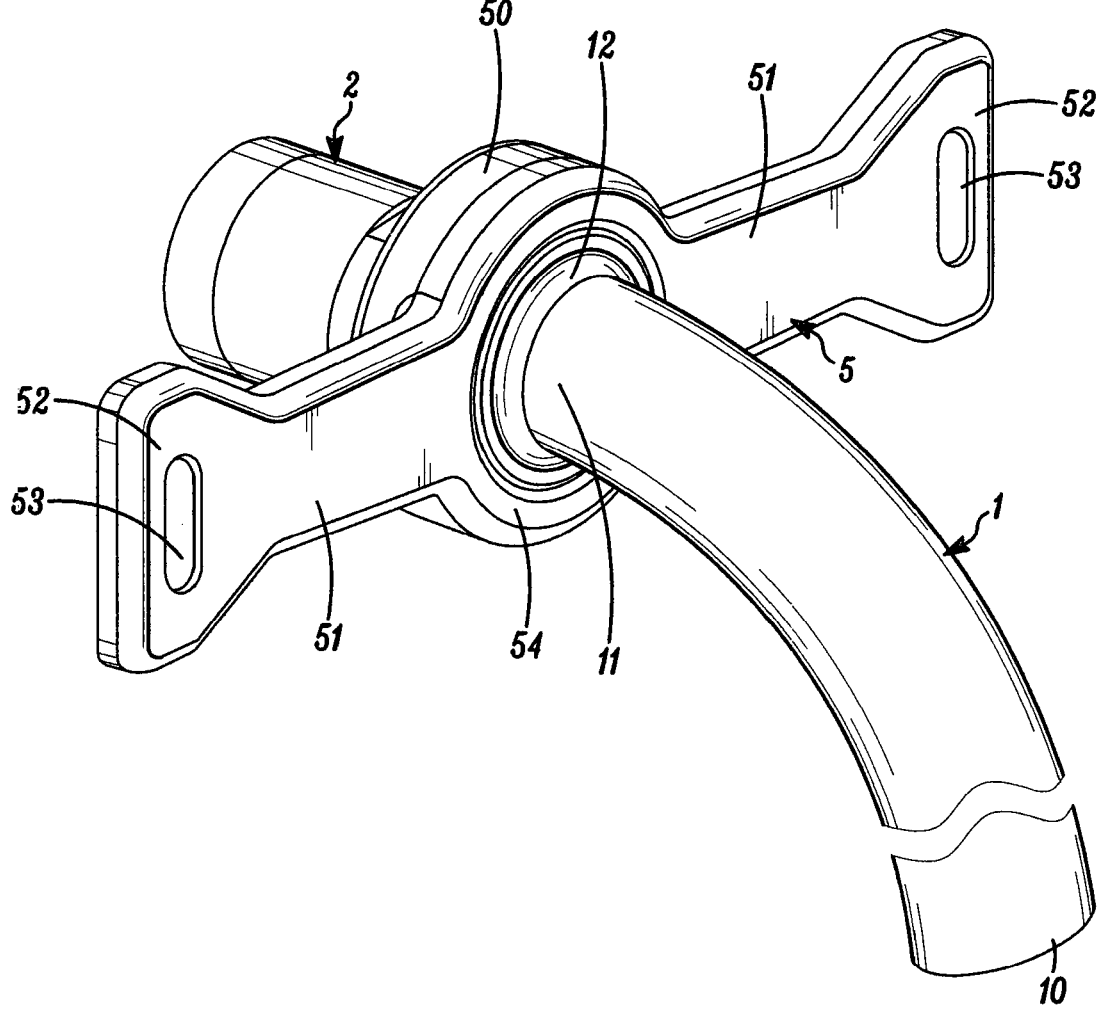
FIG. 1 is a perspective view of the rube from its forward, patient end.
Figure 2:
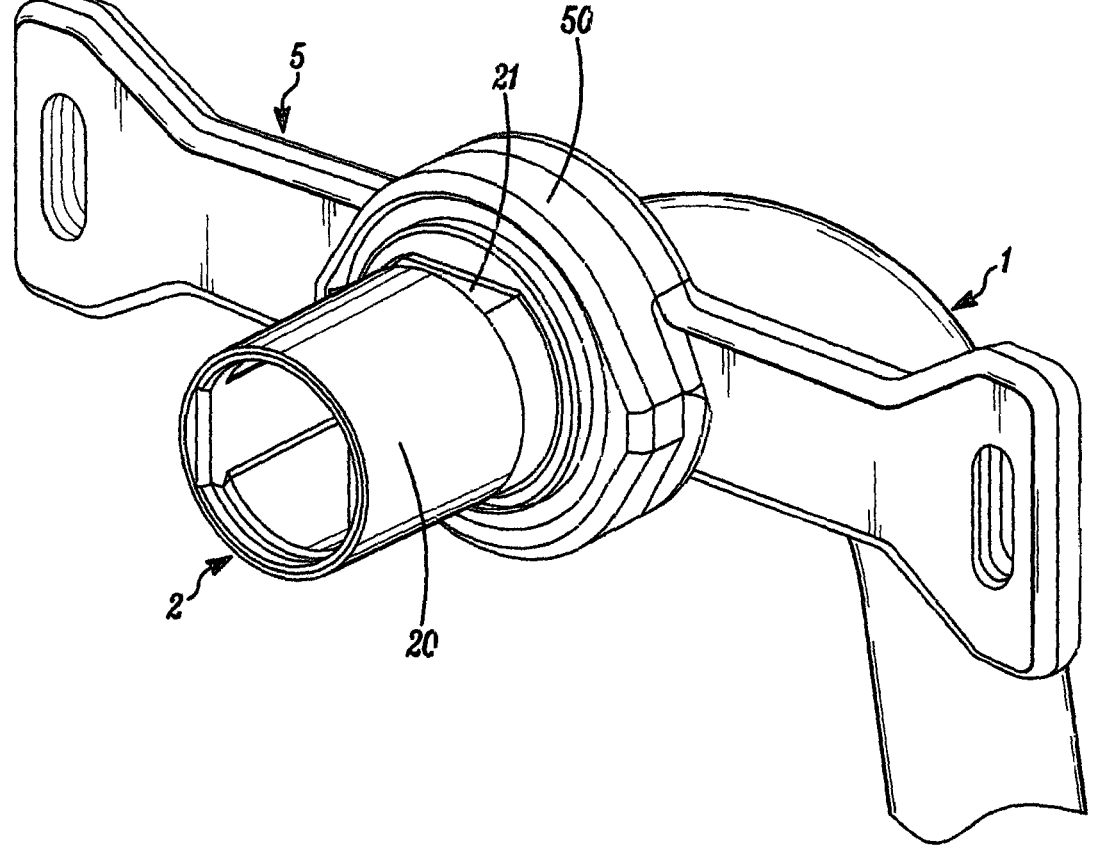
FIG. 2 is a perspective view of the tube from its rear, machine end.
Figure 3:
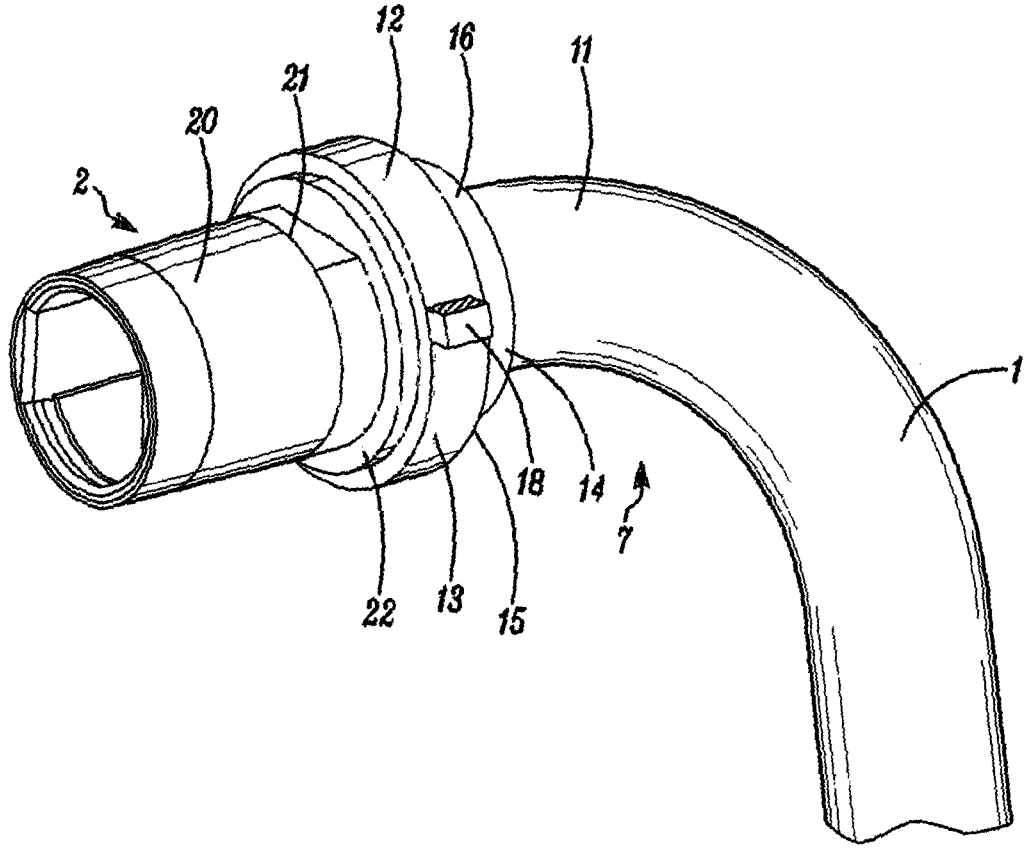
FIG. 3 is a perspective view of a sub-assembly of a shaft and connector at a preliminary stage of manufacture.
Figure 4:
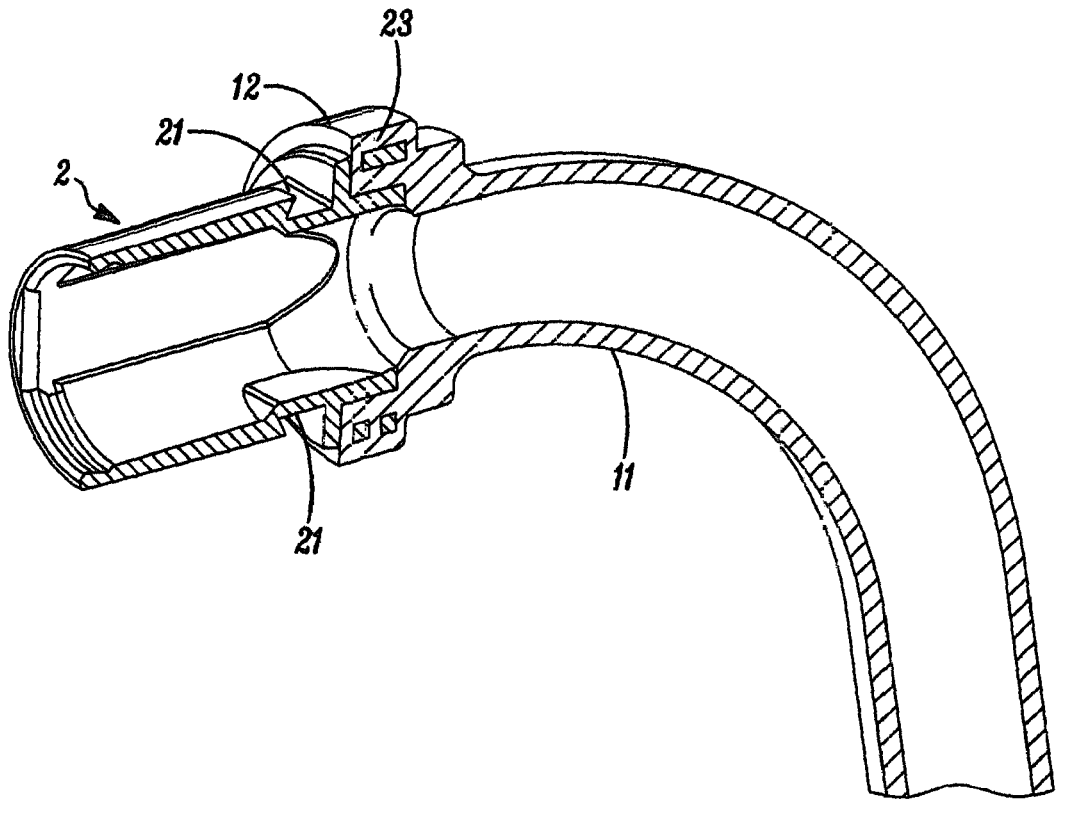
FIG. 4 is a cut-away view along the axis of the sub-assembly shown in FIG. 3.
Figure 5:
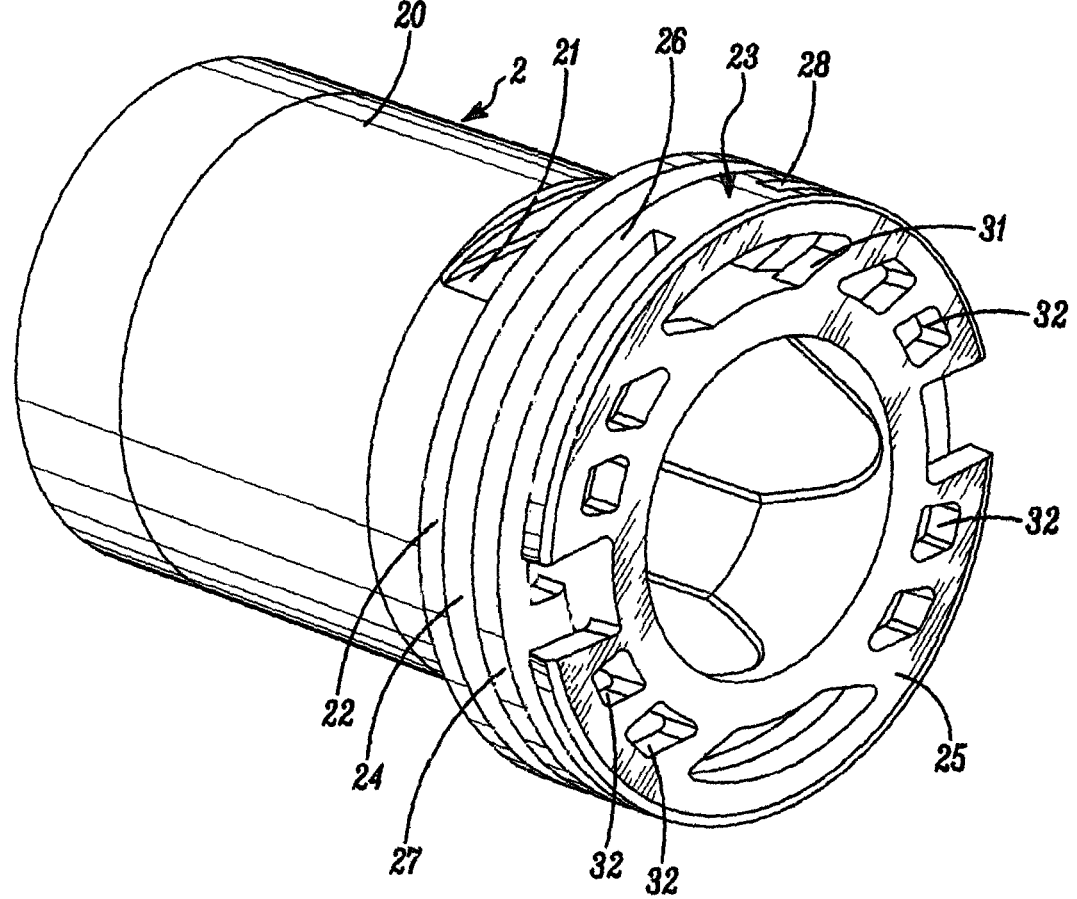
FIG. 5 is an enlarged perspective view of the connector before moulding with the shaft.
Figure 6:
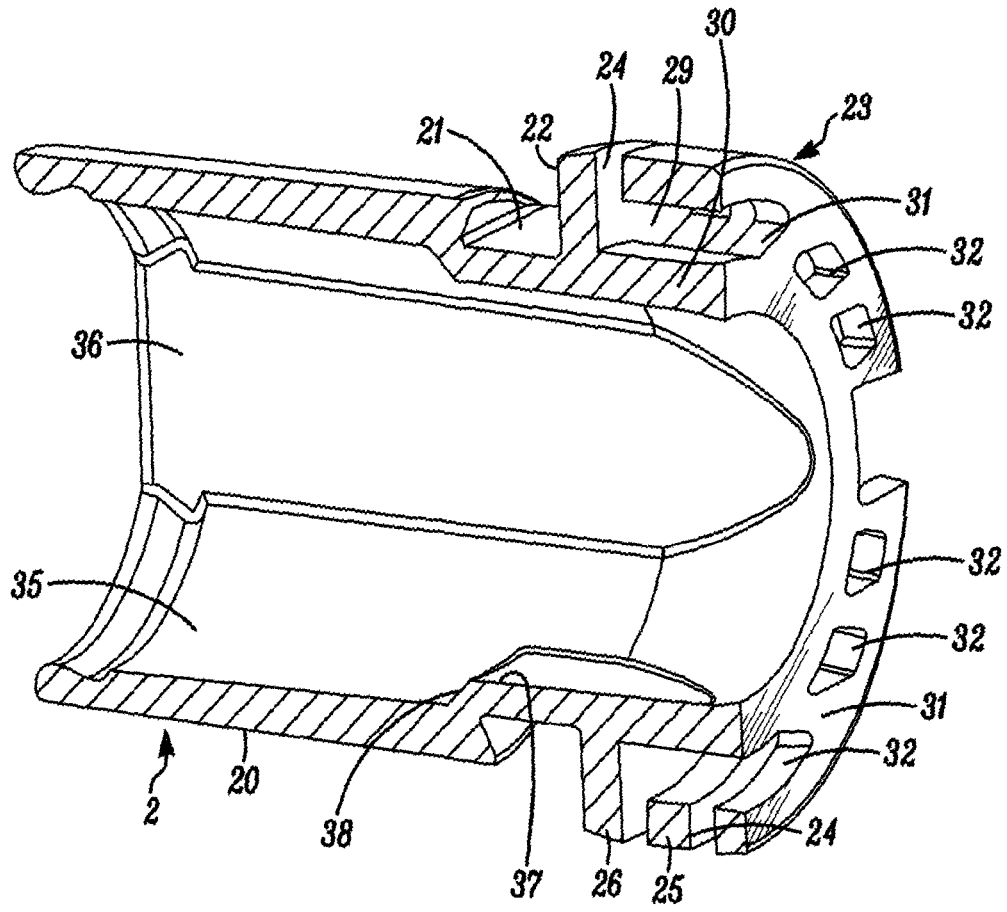
FIG. 6 is cut-away view along the axis of the connector shown in FIG. 5.

With reference first to FIGS. 1 and 2, the tube is formed of three components joined with one another, namely a shaft 1 providing a gas passage to the trachea, a connector or coupling 2, which may also be referred to as coupling 2 or connector 2, for enabling gas connection with the shaft, and a flange 5 for securing the tube with the patient's neck.

The shaft 1 is moulded of a silicone or other relatively soft plastics material with a circular cross-section and is curved along its length. The forward, patient end 10 of the shaft 1 is adapted for location in the patient's trachea. The rear, machine end 11, which may also be referred to as machine end 11 or rear end 11, of the shaft is adapted to extend through the tracheostomy opening and to project from the surface of the neck. The machine end 11 is moulded with an externally enlarged boss 12, which may also be referred to as boss 12, enlarged boss 12 or rear end boss 12, that will be described in detail later. The shaft 1 is shown without any sealing cuff but any conventional sealing cuff and inflation line could be provided. The shaft 1 could have alternative shapes and sections, and could be made of other materials.

With reference now also to FIGS. 3 to 8, the connector or coupling 2 is moulded of a relatively hard plastics material such as polysulphone and has a tubular shape with a generally circular section. The greater part of the length of the connector 2 is provided by an externally-tapered coupling portion 20 that forms a male mating surface adapted to fit within a cooperating female tapered coupling at the end of a breathing tube (not shown). Externally, at the patient end of the coupling portion 20, the connector is formed with two flat faces 21 arranged parallel and diametrically opposite one another, facing outwardly of the coupling 2. A circular flange portion 22 projects outwardly around the connector 2 on the patient side of the flat faces 21 and has a diameter slightly larger than that of the coupling portion 20. A retaining formation including a ring structure 23 of the same diameter as the flange 22 but about twice its width is spaced a short distance forwardly of the flange to form an annular cavity 24 on the patient side, which may be referred to as the patient end, of the flange. The ring structure 23 is divided into a forward and rearward disc 25 and 26 by two annular, part-circular slots 27 and 28 opening both externally of the ring structure and internally into an annular recess 29 extending around an inner tubular patient end portion 30 of the connector 2. The discs 25 and 26 are supported on the inner tubular patient end portion 30 by a number of outwardly-extending struts 31 spaced around the connector 2, which are separated from one another by a number of apertures 32 opening into the annular recess 29 and the annular cavity 24. The slots, apertures, recesses and cavities 27, 28, 29, 24 and 32 together may be referred to as the rear end or patient end retaining formation, or simply the retaining formation, of the ring structure 23. The purpose of these slots, apertures, recesses and cavities 27, 28, 29, 24 and 32 is to form flow paths that enable plastics material from the rear end boss 12 of the shaft 1 to flow around the rear end retaining formation of the ring structure 23 of the connector 2 and form a secure mechanical interlocking of the shaft with the connector, despite the different properties of the materials of the shaft and connector. The combination of the shaft 1 with the connector 2 forms a subassembly 7.

Forwardly of the rear end step 13, which may also be referred to as the end 13, on the boss 12 of the shaft 1 is an intermediate annular step 14, which may also be referred to as annular step 14 or intermediate step 14, the diameter of which is slightly less than the external diameter of the ring structure 23 so that a forwardly-facing, radial, annular abutment surface or wall 15, which may also be referred to as annular surface 15 or annular abutment wall 15, is formed between the two steps. The intermediate step 14 has a larger diameter than the outside of the main part of the shaft 1 so that a second, forward wall 16 is formed between this step and the rear end 11 of the shaft. The external surface of the rear end step 13 is also formed with two short location lugs 18 (only one visible in FIG. 3) of generally rectangular shape that project radially outwardly diametrically opposite one another and aligned along an axis orthogonal to both the axis of the connector 2 and the plane of curvature of the shaft 1.

The internal surface 35 of the connector 2 has a circular section the diameter of which is reduced slightly along a forward patient end portion 37. The step 38 between the forward portion 37 and the rear part of the surface 35 is tapered to form a part-annular incline. The internal surface 35 of the connector is also interrupted by two parallel longitudinally extending flats 36 arranged parallel to one another. The flats 36 form keys to ensure that only an inner cannula (not shown) with a corresponding keyway on its machine end fitting can be fitted fully in the tracheostomy tube.

Figure 7:
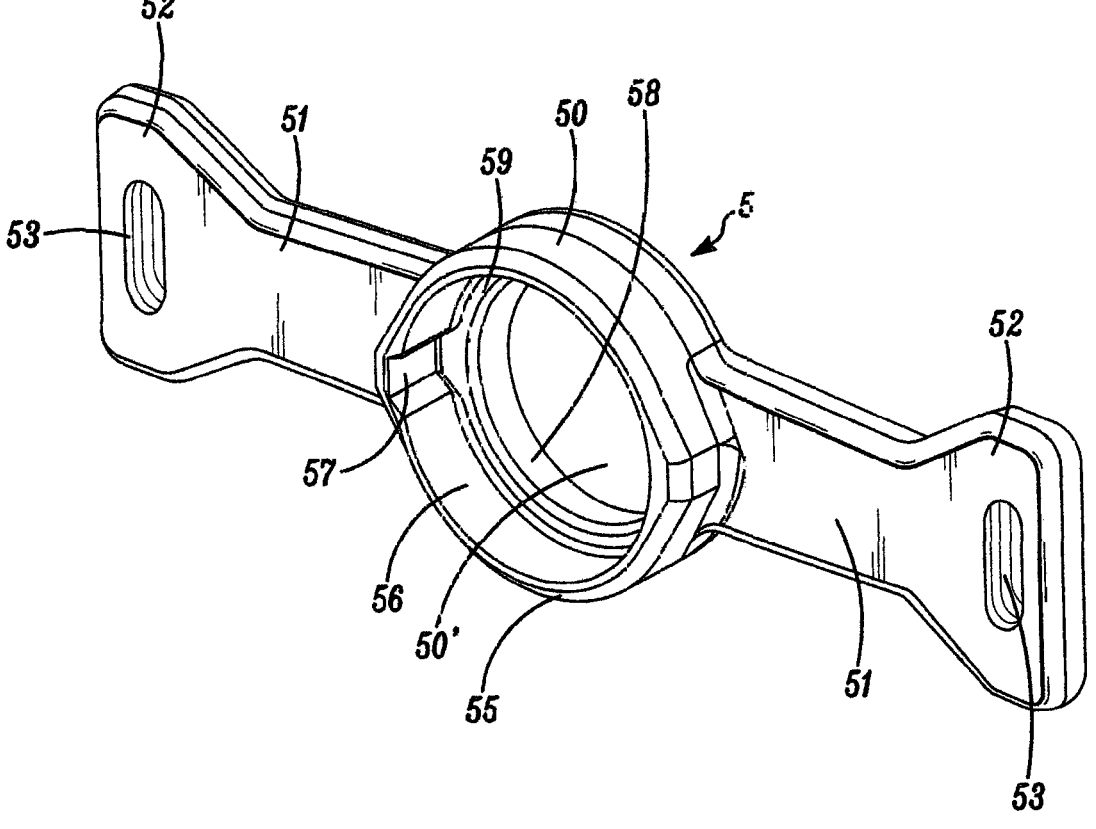
FIG. 7 is a perspective view of the flange before assembly.
Figure 8:
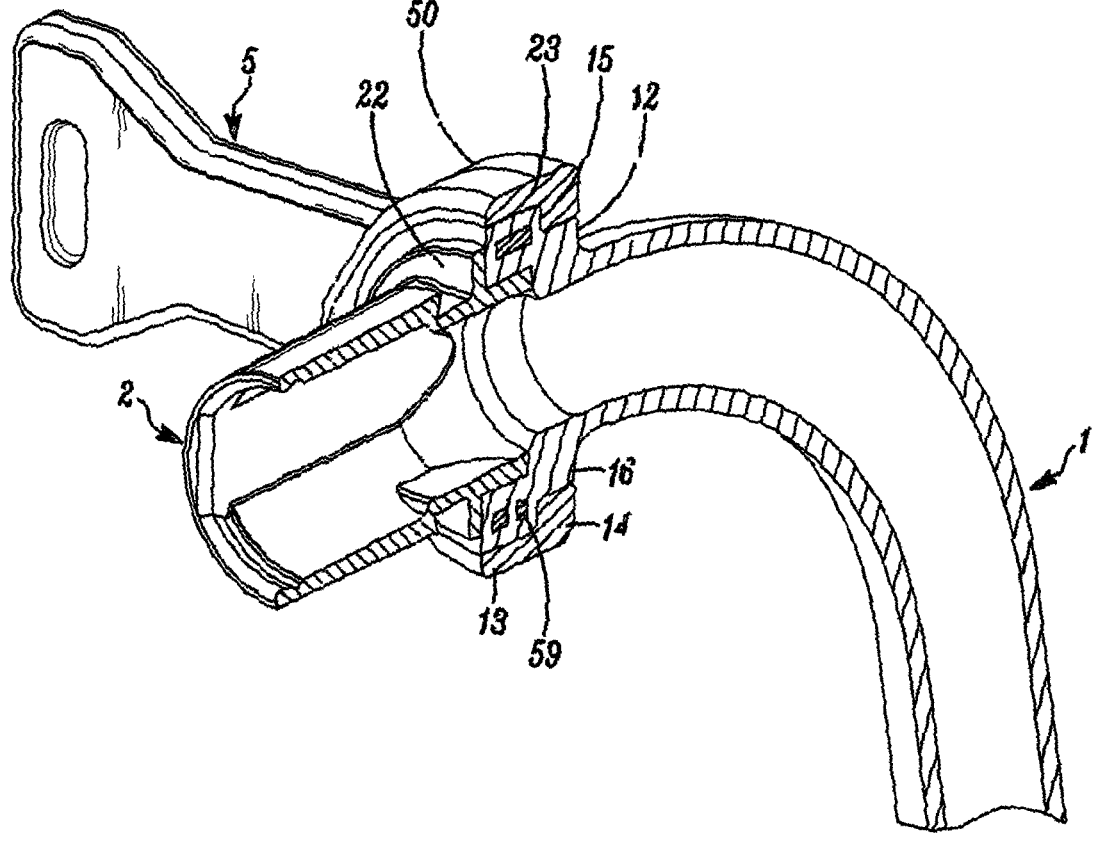
FIG. 8 is a cut-away view of the tube from its rear, machine end.

The third component of the tube is the flange 5, shown most clearly in FIGS. 1 and 7. This is moulded from a soft, flexible plastics, such as silicone, and may be the same as the material of the shaft 1. The flange 5 has a central collar 50 providing an attachment portion for attaching with the shaft 1. Two arms 51 extend radially outwardly on opposite sides of the collar 50 and are terminated at their outer ends by enlarged lugs 52. Each lug 52 has a slot 53 formed through its thickness to receive a neck strap (not shown) by which the tube is secured around the patient's neck. The patient end surface 54 of the collar 50 is level and continuous with the patient surface of the arms 51. The length or thickness of the collar 50 is greater than the thickness of the flange 5 so that the rear, machine end 55 of the collar projects beyond the rear surface of the flange. The length of the collar 50 is selected to be equal to the length of the enlarged boss 12 at the rear end of the shaft 1. The inside or opening 50' of the collar 50 includes a rear, machine end portion 56 having a diameter equal to the external diameter of the rear end step 13 of the shaft and connector sub-assembly. The machine end internal portion 56 is interrupted by two location notches 57 of rectangular section located diametrically opposite one another along an axis parallel with the length of the two arms 51. The notches 57 extend longitudinally of the length of the machine end portion 56. The internal machine end portion 56 is divided from an internal patient end portion 58 by a rearwardly-facing annular abutment surface or wall 59, which may simply be referred to as rearwardly-facing surface 59 or the rearwardly-facing wall 59, around the opening 50'. The diameter of the internal patient end portion 58 of the flange 5 is equal to the external diameter of the intermediate annular step 14 on the shaft 1. The internal dimensions and configuration of the collar 50 of the flange 5 and the external dimensions and configuration of the boss 12 on the shaft 1 are such that the boss fits snugly within the collar with the forward-facing annular surface 15 on the boss abutting the rearward-facing annular surface 59 in the collar. The two lugs 18 at the rear end of the shaft 1 align with and locate in the two notches 57 in the collar 50 of the flange 5 so as to ensure that the arms 51 of the flange extend orthogonally to the plane of curvature of the shaft.

The tube is made by initially separately moulding the connector 2 and flange 5 as discrete components of different plastic compositions. The connector 2 is then placed in a mould tool having a cavity defining the shape of the shaft. Flowable plastics material is then injected into the cavity so that it flows along the part defining the shape of the shaft and also flows around the retaining ring structure 23 of the connector 2. The material of the shaft 1 is softer and has a lower melt temperature than that of the connector 2. When the shaft material has fully cured the sub-assembly of connector 2 and shaft 1 is removed from the mould tool as the subassembly 7. The next step is to apply a bonding agent such as a solvent or adhesive to the inner surface of the collar 50 on the flange 5 and to the outer surface of the boss 12 on the connector and shaft sub-assembly. The patent end 10 of the shaft 1 is then extended through the collar 50 of the flange 5 and the flange is threaded along the shaft until the boss 12 on the shaft enters the collar. At this stage the flange 5 is appropriately oriented so that the lugs 18 on the outside of the boss 12 align with the notches 57 in the collar 50, thereby ensuring that the flange is appropriately oriented with respect to the plane of curvature of the shaft. After the bonding agent has fully cured the tube is ready for use or for any finishing operations.

The moulded connection between the shaft and the connector ensures an effective gas and liquid seal between these two components and also ensures an effective mechanical interlocking between the shaft and the connector. This prevents any risk these components could separate. The engaging surfaces 59 and 15 on the flange 5 and the boss 12 of the shaft 1 also ensure that, even if the bond between them should break down, there would be no risk that the subassembly 7 could separate from the flange and displace into the patient The tube also has various manufacturing advantages. Tracheostomy tubes are provided in a range of different sizes for patients of different builds and anatomies, but the flange usually has the same size across the entire range from neonatal, paediatric to adult patients. By forming the flange as a separate component, it is possible for the same flange to be used across the entire range of sizes, thereby enabling more effective inventory management. Also, forming the flange separately from the shaft means that they could be made of different materials with different properties. The lug and notch features on the flange and the boss of the shaft ensure that the flange can only be mounted on the tube at the correct orientation, thereby preventing incorrect assembly and possible waste. One conventional manufacturing technique involves moulding the shaft and flange together as a single component. The problem with this is that the flange and shaft extend in different planes leading to large and expensive mould tools. By forming the flange separately from the shaft smaller and lower cost mould tools can be used, thereby enabling the cost of manufacture to be minimized.

The invention claimed is:

1. A tracheostomy tube comprising a shaft for providing a gas passage to the trachea, a coupling for enabling gas connection with the shaft, and a flange adapted to secure the tracheostomy tube with a patient's neck, characterised in that the coupling is of a harder material than the shaft, that the rear, machine end of the shaft is attached with the coupling by material of the shaft flowed around a retaining formation at the patient end of the coupling such that the coupling and the shaft are mechanically interlocked to each other to form a subassembly when the material of the shaft is cured, that an external surface at the rear end of the subassembly is formed with an abutment surface facing towards the forward, patient end of the tracheostomy tube, and that the flange has an attachment portion with an abutment surface facing rearwardly, the abutment surface on the flange abutting the abutment surface on the subassembly so as to prevent forward movement of the subassembly relative to the flange, wherein the retaining formation comprises a ring structure that includes two discs spaced from one another along and around the forward end of the coupling, and wherein the material of the shaft is flowed in and around the two discs.

2. A tracheostomy tube according to claim 1, characterised in that the two discs are spaced from one another by an annular cavity, and that the forward disc is formed with a plurality of apertures opening through the disc into the cavity.

3. A tracheostomy tube according to claim 1, characterised in that flange is bonded with the abutment surface on the subassembly.

4. A tracheostomy tube according to claim 1, characterised in that the abutment surface at the rear end of the subassembly is provided by an externally-enlarged boss formed with a locating lug arranged to locate in a notch formed in the flange.

5. A tracheostomy tube according to claim 1, characterised in that shaft is of a silicone material.

6. A tracheostomy tube according to claim 1, characterised in that the flange is of a silicone material.

7. A tracheostomy tube according to claim 1, characterised in that the coupling is of polysulphone.

8. A method of manufacturing a tracheostomy tube comprising:

moulding a coupling of a relatively hard material to include a retaining formation comprising a ring structure having two discs spaced from one another around a forward, patient end of the coupling;

moulding a shaft of a softer material onto the coupling so that the softer material at the rear, machine end of the shaft flows in and around the two discs of the retaining formation to form a subassembly by mechanical interlocking of the shaft with the coupling, the external surface of the rear end of the subassembly being formed with an abutment surface facing forwardly;

providing a flange having an attachment portion with an opening and an abutment surface around the opening facing rearwardly;

threading the opening on the flange along the shaft from its patient end to its machine end until the abutment surface on the flange abuts the abutment surface on the subassembly; and bonding the flange to the shaft with the engagement of the abutment surfaces and preventing forward movement of the subassembly relative to the flange.

9. A tracheostomy tube manufactured by the process of:

moulding a coupling of relatively hard material to include a retaining formation comprising a ring structure having two discs spaced from one another around a forward, patient end of the coupling;

moulding a shaft of a softer material onto the coupling so that the softer material at the rear, machine end of the shaft flows in and around the two discs of the retaining formation to form a subassembly by mechanical interlocking of the shaft with the coupling, the external surface of the rear end of the subassembly being formed with an abutment surface facing forwardly;

providing a flange having an attachment portion with an opening and an abutment surface around the opening facing rearwardly;

threading the opening on the flange along the shaft from its patient end to its machine end until the abutment surface on the flange abuts the abutment surface on the subassembly; and bonding the flange to the shaft with the engagement of the abutment surfaces and preventing forward movement of the subassembly relative to the flange.

* * * * *